United States Patent [19]

Ainsworth et al.

[11] 4,338,333
[45] Jul. 6, 1982

[54] ETHANAMINE DERIVATIVES THEIR PREPARATION AND USE IN PHARMACEUTICAL COMPOSITIONS

[75] Inventors: Anthony T. Ainsworth, Cranleigh; David G. Smith, Redhill, both of England

[73] Assignee: Beecham Group Limited, England

[21] Appl. No.: 157,555

[22] Filed: Jun. 9, 1980

[30] Foreign Application Priority Data

Jun. 16, 1979 [GB] United Kingdom ............... 7921038

[51] Int. Cl.³ .................. A61K 31/24; C07C 101/30
[52] U.S. Cl. .............................. 424/309; 424/319; 424/321; 424/322; 424/324; 424/316; 560/12; 560/13; 560/21; 560/34; 560/42; 562/430; 562/435; 562/439; 562/451; 564/51; 564/99; 564/162; 564/165
[58] Field of Search .............. 560/42, 21, 34, 12, 560/13; 562/451, 435, 439, 430; 564/165, 51, 99, 162; 424/309, 319, 322, 324, 316, 321

[56] References Cited

U.S. PATENT DOCUMENTS 4,012,444 3/1977 Lunts et al. ..................... 562/451
4,146,638 3/1979 Renth et al. ..................... 560/42

OTHER PUBLICATIONS

Kamiya et al., Chem. Absts., 84, 164461(m) (1976).

Primary Examiner—G. T. Breitenstein
Attorney, Agent, or Firm—Jacobs & Jacobs

[57] ABSTRACT

The compounds of formula (II):

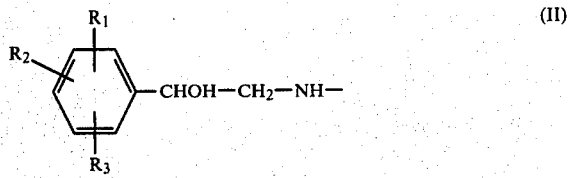

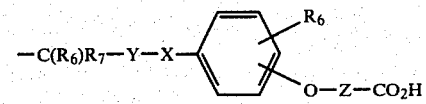

in which $R_1$ is a hydrogen, fluorine, chlorine or bromine atom or a hydroxyl, hydroxymethyl, methyl, methoxyl, amino, formamido, acetamido, methylsulphonylamido, nitro, benzyloxy, methylsulphonylmethyl, ureido, trifluoromethyl or p-methoxybenzylamino group; $R_2$ is a hydrogen, fluorine, chlorine or bromine atom or a hydroxyl group; $R_3$ is a hydrogen, chlorine or bromine atom or a hydroxyl group, $R_4$ is a hydrogen atom or a methyl group; $R_5$ is a hydrogen atom or a methyl group; $R_6$ is a hydrogen, fluorine or chlorine atom or a methyl, methoxyl or hydroxy group; X is an oxygen atom or a bond; Y is an alkylene group of up to 6 carbon atoms or a bond; and Z is an alkylene, alkenylene or alkynylene group of up to 10 carbon atoms, have been found to possess anti-obesity and/or anti-hyperglycaemic activity.

16 Claims, No Drawings

ETHANAMINE DERIVATIVES THEIR PREPARATION AND USE IN PHARMACEUTICAL COMPOSITIONS

The present invention relates to a group of secondary amine derivatives that possess anti-obesity and anti-hyperglycaemic properties, to the method of their preparation and to their use as anti-obesity and/or anti-hyperglycaemic agents when formulated into a pharmaceutical composition.

Certain of the compounds within the formula (I):

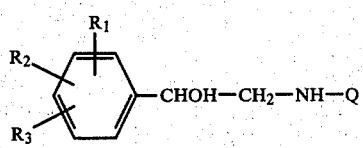

wherein $R_1$ is a hydrogen, fluorine or chlorine atom or a hydroxyl, hydroxymethyl, methyl, methoxyl, amino, formamido, acetamido, methylsulphonylamido, nitro, benzyloxy, methylsulphonylmethyl, ureido, trifluoromethyl or p-methoxybenzylamino group; $R_2$ is a hydrogen, fluorine or chlorine atom or a hydroxyl group; $R_3$ is a hydrogen or chlorine atom or a hydroxyl group; and Q is an isopropyl or t-butyl group; are known to possess β-adrenoceptor agonist activity (see for example D. T. Collins et al, J. Med. Chem., 1970, 13, 674). Certain compounds within formula (I) wherein Q is a group such as a phenylaminoethyl were disclosed in Belgian Pat. No. 851232 as possessing β-adrenoceptor stimulant activity. Belgian Pat. No. 809831 disclosed that certain compounds within formula (I) wherein Q is inter alia a substituted phenylethyl group are useful as medicaments for the treatment of skin diseases. U.S. Pat. No. 3,818,101 disclosed certain compounds within formula (I) wherein Q could be inter alia an aralkyl group which may be used to induce polyphagia in meat producing animals. Certain compounds within the formula (I) wherein Q may be hydroxybenzyl or alkoxybenzyl group were indicated as possessing β-adrenergic stimulant and blocking properties in South African Patent No. 67/5591. The preceding publications do not describe compounds of the formula (I) as possessing anti-obesity activity coupled with anti-hyperglycaemic activity nor indeed do they describe compounds of the formula (I) as possessing anti-obesity activity alone. We have discovered a group of compounds somewhat related to those of the formula (I) which possess anti-obesity properties and/or anti-hyperglycaemic properties. Such compounds may thus be used in the treatment of obesity or hyperglycaemia and can be envisaged as being of particular interest in conditions such as maturity onset diabetes where obesity is often linked with hyperglycaemia.

The present invention provides the compounds of the formula (II):

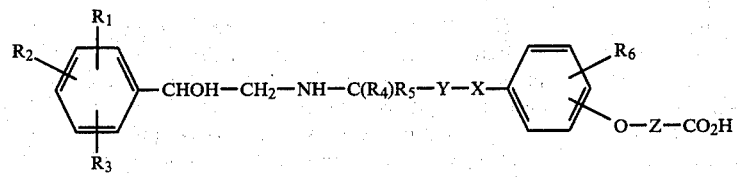

or a pharmaceutically acceptable salt, ester or amide thereof wherein $R_1$, $R_2$ and $R_3$ are as defined in relation to formula (I) or each independently represent a bromine atom; $R_4$ is a hydrogen atom or a methyl group; $R_5$ is a hydrogen atom or a methyl group; $R_6$ is a hydrogen, fluorine or chlorine atom or a methyl, methoxyl or hydroxy group; X is an oxygen atom or a bond; Y is an alkylene group of up to 6 carbon atoms or a bond; and Z is an alkylene, alkenylene or alkynylene group of up to 10 carbon atoms.

The —O—Z—CO$_2$H moiety is preferably attached para- to the —X— moiety.

Preferred values for $R_1$ include the hydrogen, fluorine, chlorine and bromine atoms and the trifluoromethyl, hydroxymethyl, hydroxyl and amino groups.

Suitably X in the compounds of the formula (II) is a bond.

Preferred groups Y are of the formula —(CH$_2$)$_n$— where n is an integer from 1 to 5, particularly 1 or 2.

A particularly suitable value for each of $R_2$ and $R_3$ is the hydrogen atom.

Particularly suitable groups $R_1R_2R_3C_6H_2$ include the phenyl; 2-fluorophenyl; 3-trifluoromethylphenyl; 3-chlorophenyl, 3,5-dichloro-4-aminophenyl; 2-chlorophenyl; 3-hydroxymethyl-4-hydroxyphenyl; 4-chlorophenyl; 3-bromophenyl and 3-fluorophenyl groups.

C(R$_4$)R$_5$ may be a CH$_2$, CHCH$_3$, or C(CH$_3$)$_2$ group, and the compounds of this invention wherein C(R$_4$)R$_5$ is a CH$_2$ or C(CH$_3$)$_2$ group tend to be less potent as anti-obesity agents than those wherein C(R$_4$)R$_5$ is a CH(CH$_3$) group. Since, however, they possess one less centre of asymmetry they offer the advantage of a slightly easier synthesis. The compounds wherein C(R$_4$)R$_5$ is a CH(CH$_3$) group offer the considerable advantage of higher potency as anti-obesity agents.

In accordance with convention usage, the terms "alkenylene" and "alkynylene" do not extend to systems containing an oxygen atom attached to the carbon of a carbon-carbon double bond.

The group Z may be branched, for example to carry one or two methyl groups, but it is more suitably unbranched. Aptly the group Z contains 1 to 6 carbon atoms and more suitably 1 to 4 carbon atoms.

Groups Z include CH$_2$, CH$_2$CH$_2$, CH$_2$CH$_2$CH$_2$, CH$_2$CH$_2$CH$_2$CH$_2$, CH$_2$CH=CH.

A particularly favoured group Z is the CH$_2$ group.

Certain especially favoured compounds of the invention are these esters of the compounds of the formula (II) hydrolysed in-vivo to yield the corresponding compound of the formula (II) per se or its salt.

Particularly suitable in-vivo hydrolysable esters include lower alkyl groups, lower alkyl groups substituted by a hydroxyl group not on the α-carbon atom and groups of the sub-formulae (a) or (b):

$$-CHR_7-O-CO-R_8 \qquad (a)$$

-continued (b)

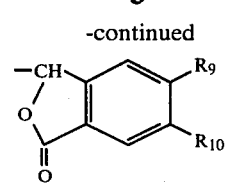

wherein $R_7$ is a hydrogen atom or a methyl group; $R_8$ is a lower alkyl or phenyl group; $R_9$ is a hydrogen atom or a methyl or methoxyl group; and $R_{10}$ is a hydrogen atom or a methyl or methoxyl group.

Certain particularly suitable esters include the methyl, ethyl, propyl and butyl esters, for example the methyl ester the ethyl ester and the isopropyl ester.

One group of preferred compounds of this invention are those of the formula (III):

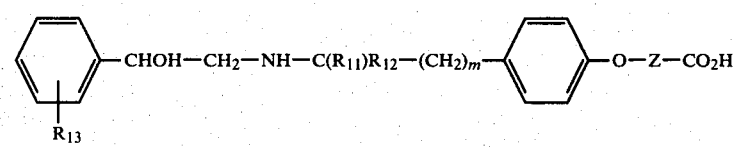

or a pharmaceutically acceptable salt, ester or amide thereof, wherein $R_{13}$ is a hydrogen, fluorine or chlorine atom or a trifluoromethyl group, Z is as defined in relation to formula (II), $R_{11}$ is a hydrogen atom or a methyl group; $R_{12}$ is a hydrogen atom or a methyl group; and m is 1, 2 or 3.

Preferably Z is a $CH_2$ group.

A further group of preferred compounds of this invention are those of the formula (IV):

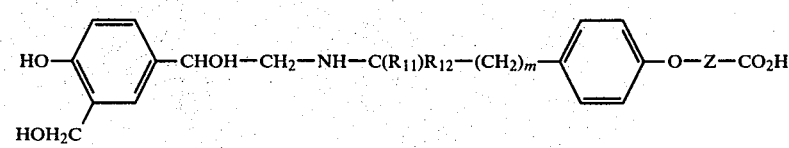

or a pharmaceutically acceptable salt, ester or amide thereof, wherein Z is as defined in relation to formula (II), $R_{11}$ is a hydrogen atom or a methyl group; $R_{12}$ is a hydrogen atom or a methyl group; and m is 1, 2 or 3.

Preferably Z is a $CH_2$ group.

Certain specific esters in relation to formulae (III) and (IV) include the methyl ethyl, n-propyl, 2-hydroxyethyl, glyceryl, acetoxymethyl, pivaloyloxymethyl, α-ethoxycarbonyloxyethyl and phthalidyl groups. Other specific values for $R_8$ include iso-propyl, n-butyl, isobutyl, t-butyl, pentyl, hexyl, benzyl and phenyl. Alkyl groups of 1 to 4 carbon atoms prove particularly convenient.

The compounds of this invention which are esterified may be provided as acid addition salts. Such salts may be of an organic or inorganic acid but are normally salts with a pharmaceutically acceptable acid. Suitable acid addition salts include those formed with acids such as hydrochloric, hydrobromic, orthophosphoric, sulphuric, methanesulphonic, toluenesulphonic, acetic, propionic, lactic, citric, fumaric, malic, succinic, salicylic, acetylsalicylic or the like acid.

The compounds of the formula (II) have a centre of asymmetry at the carbon atom marked with a single asterisk in formula (IIa):

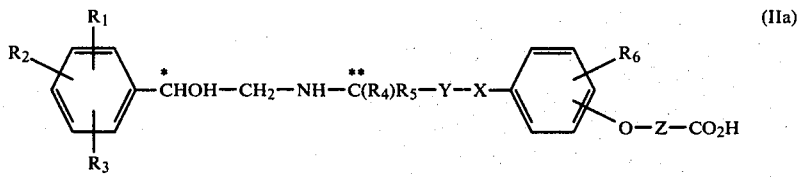

wherein $R_1$-$C_6$, X,Y and Z are as defined in relation to formula (II). The compounds of the formula (II) have another centre of asymmetry at the carbon atom marked with two asterisks in formula (IIa) when $R_4$ is different from $R_5$.

The present invention extends to the individual stereoisomeric forms of the compounds of the formula (II) as well as to mixtures thereof. Aptly those compounds of the formula (II) which contain two asymmetric centres are provided in the form of the separated diastereoisomers. Such separated diastereoisomers will of course contain a pair of compounds which are mirror images of each other.

X-Ray analysis may be used to determine and correlate absolute stereochemistry.

It has been observed that in the $^{13}C$ NMR of a compound containing a methyl group on the carbon atom α to the nitrogen atom (ie one existing in diastereoisomeric forms), the R*, R**; S*, S** diastereoisomer is that in which said methyl group appears at higher field (lower numerical value when expressed in ppm, typically <20 ppm downfield from tetramethylsilane) in $d_6$DMSO solution, whilst the lower field (higher numerical value, typically >20 ppm downfield from TMS) resonance is attributable to the R*, S**; S*, R** modification. The amount of each diastereoisomer may be estimated from the relative intensities of the absorption lines and is expressed in the examples as a ratio (R*, R**, S* S**:R* S**, S* R**). Other paired resonances can occur for the carbon atoms attached directly to the nitrogen atom and the carbon β to nitrogen which carries the hydroxyl group.

The present invention also provides a pharmaceutical composition which comprises a compound of this invention and a pharmaceutically acceptable carrier.

The compositions of this invention will normally be formulated for oral administration although compositions formulated for non-oral modes of administration, for example, injection, are also envisaged.

Particularly suitable oral dosage forms are unit dose forms such as tablets or capsules. Other fixed unit dose forms such as powders presented in sachets may also be used.

In accordance with conventional pharmaceutical practice the carrier may comprise a diluent, binder, filler, disintegrant, wetting agent, lubricant, colourant, flavourant or the like.

Typical carriers may therefore comprise such agents as microcrystalline cellulose, starch, sodium starch glycollate, polyvinylpyrrolidone, polyvinylpolypyrrolidone, magnesium stearate, sodium lauryl sulphate, sucrose and the like.

Most suitably the composition will be provided in unit dose form. Such unit doses will normally comprise 0.01 to 500 mg, more usually 0.2 to 100 mg and favourably 0.5 to 50 mg. Such doses may be taken one to six times a day in a manner such that the total daily dose for a 70 kg adult will generally be about 0.1 to 500 mg and more usually about 1 to 100 mg. The more potent preferred compounds will generally be in unit doses containing 0.1 to 10 mg, more usually 0.25 mg to 5 mg. Their daily dose will generally be about 0.5 to 20 mg, more usually 1 to 10 mg, for example 2 to 5 mg.

In addition to use in human medicine the compositions of this invention may be used to treat obesity in domestic mammals such as dogs. In general administration to domestic mammals may be by mouth and will usually take place one or two times a day at about 0.025 mg/kg to 25 mg/kg, for example 0.1 mg/kg to 5 mg/kg.

The present invention also provides a process for the preparation of a compound of this invention which comprises the reduction of a compound of the formula (V):

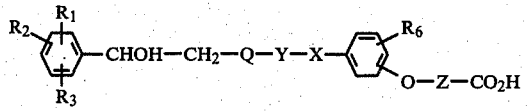

or its ester or amide wherein Q is a $-N=CR_4$ or $-NH-C(OH)R_4-$ group and $R_1, R_2, R_3, R_6$, X and Y and Z are as defined in relation to formula (II) and thereafter if desired forming an addition salt of the initially produced compound of the formula (II).

The reduction of the compound of formula (V) may be normally effected by catalytic hydrogenation. Suitable catalysts include noble metal catalysts such as palladium, for example palladium on charcoal or the like such as platinum for example as platinum oxide.

If platinum is used as catalyst an atmospheric pressure of hydrogen may be employed. The reaction may be carried out at any convenient nonextreme temperature but it is generally most suitable to use an ambient or a slightly super ambient temperature such as 30° C. to 100° C., for example 40° C. to 80° C. The hydrogenation may be carried out in a conventional hydrogenation solvent such as a lower alkanol, for example ethanol.

The desired compound may be isolated from the reaction mixture by evaporation of the filtered solution. The initially obtained product may be purified by conventional means, for example by chromatography, crystallisation or the like.

The reduction of the compound of the formula (V) may also be effected using a complex hydride such as sodium borohydride.

This reduction is generally carried out in a lower alkanolic solvent, for example methanol if a methyl ester is desired. An approximately ambient temperature may be employed, for example 20° to 30° C.

The desired compound may be obtained from the reaction mixture by evaporation, extraction into a suitable solvent such as ethyl acetate and evaporation. The initially obtained product may be purified as outlined hereinbefore.

The compound of the formula (V) may be prepared by the reaction of a compound of the formula (VI):

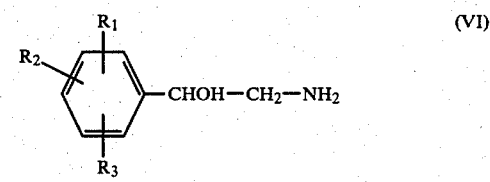

wherein $R_1$, $R_2$ and $R_3$ are as defined in relation to formula (II) with an ester or amide of a compound of the formula (VII):

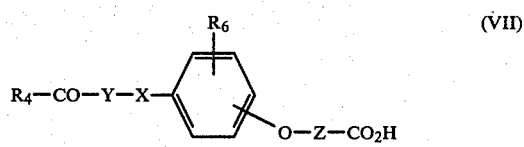

wherein $R_4$, $R_6$, Y, X and Z are as defined in relation to formula (II) and thereafter de-esterifying if desired.

The condensation reaction is generally carried out under conditions that result in the removal of water formed during the reaction. A convenient method is to remove azeotropically the water from a refluxing benzene solution using a Dean and Stark apparatus.

It is often convenient to prepare and utilize the compound of the formula (V) in situ without isolation. In this case the reaction may comprise the hydrogenation of a mixture of a compound of the formula (VI) and a compound of the formula (VII) wherein $R_1$, $R_2$, $R_3$, $R_4$, $R_6$, X, Y and Z are as defined in relation to formula (II).

Such a hydrogenation may be carried out under conditions as described for the hydrogenation of a compound of the formula (V).

The compounds of the formula (II) as hereinbefore defined may also be prepared by the reaction of a compound of the formula (VIII):

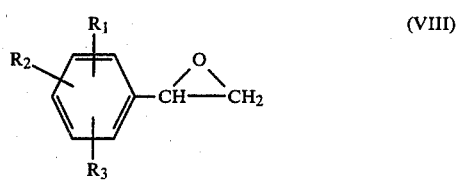

wherein $R_1$, $R_2$ and $R_3$ are as defined in relation to formula (II) with an ester or amide of a compound of the formula (IX):

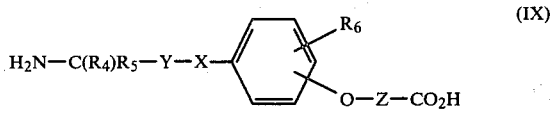

wherein $R_4$, $R_5$, $R_6$, X, Y and Z are as defined in relation to formula (II) and thereafter de-esterifying if desired.

This reaction may be carried out in a protic solvent such as a lower alkanol, preferably ethanol.

A further method of preparing the compounds of the formula (II) comprises the reduction of an ester or amide of a compound of the formula (X):

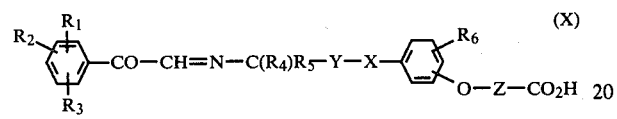

wherein $R_1$, $R_2$, $R_3$, $R_4$, $R_5$, $R_6$, X, Y and Z are as defined in relation to formula (II) and thereafter de-esterifying if desired.

The reduction of the compound of the formula (X) may be carried out using a borohydride or the like as described for the reduction of the compound of the formula (V).

The compound of the formula (X) may be prepared by the reaction of a compound of the formula (X I):

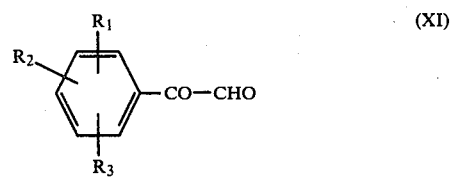

or its hydrate or hemi-acetal of a lower alkanol wherein $R_1$, $R_2$ and $R_3$ are as defined in relation to formula (II), with a compound of the formula (IX) as hereinbefore defined.

The preceding reaction is generally carried out under the same conditions as that between compounds of formulae (VI) and (VII) i.e. with azeotropic removal of water using a Dean and Stark apparatus.

The compound of the formula (X) may be obtained from the reaction mixture by evaporation of the solvent and is normally used without further purification.

Another method of preparing the compounds of the formula (II) comprises the hydrogenation of a compound of the formula (XII):

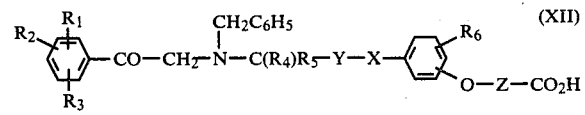

as its ester or amide wherein $R_1$, $R_2$, $R_3$, $R_4$, $R_5$, $R_6$, X, Y and Z are as defined in relation to formula (II).

The hydrogenation of the compound of the formula (XII) may take place as described for hydrogenation of the compound of the formula (V).

The compound of the formula (XII) may be prepared by the reaction of a compound of the formula (XIII):

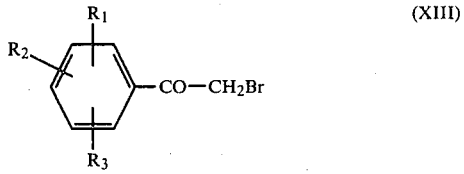

wherein $R_1$, $R_2$ and $R_3$ are as defined in relation to formula (II) with the N-benzyl derivative of a compound of the formula (IX).

This reaction may be carried out in a solvent such as acetonitrile or butanone at an elevated temperature, for example under reflux. An acid acceptor is generally present during the reaction for example a tertiary amine which may be a further mole of the N-benzyl derivative of the compound of the formula (IX).

After completion, the reaction mixture may be diluted with ether, filtered and the filtrate evaporated.

Another method of preparing compounds of formula (II) comprises reducing a compound of formula (XIV):

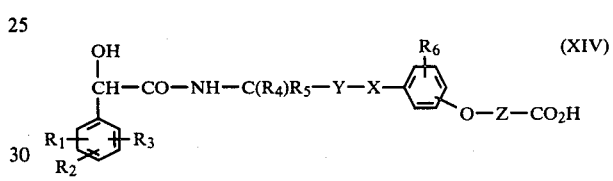

or a pharmaceutically acceptable salt, ester or amide thereof, in which $R_1$ to $R_6$, X, Y and Z as defined in formula (II). This reduction may conveniently be carried out by using a complex metal hydride or diborane.

Compounds of formula (XIV) may be prepared by reacting a compound of formula (XV):

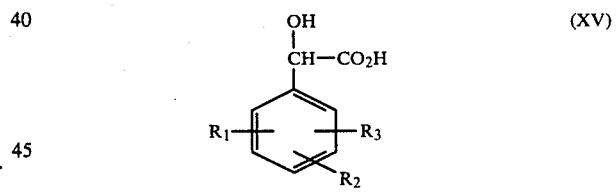

in which $R_1$, $R_2$ and $R_3$ are as defined in formula (II) with a compound of formula (IX) as defined above. The reaction may take place under standard peptide formation reaction conditions, for example in the presence of dicyclohexylcarbodi-imide, 1-hydroxybenztriazole and dimethylformamide.

By using single enantiomers of the compound of formulae (XV) and (IX) a stereospecific synthesis of single enantiomers of formula (II) can be achieved.

Groups $R_1$, $R_2$, $R_3$ and $O-Z-CO_2H$ or its ester or amide may be modified after the preceding reactions if required; for example a benzyloxy group can be converted to a hydroxy group by hydrogenation, an ester can be hydrolysed to an acid, a benzyl ester can be hydrogenated to yield an acid, a salt of an acid can be esterified by reaction with a reactive chloride, bromide or tosylate, an acid can be esterified by reaction with a hydroxy compound under dehydrating conditions, amides may be prepared from an acid via an acid chloride or similar reaction.

Compounds of the formula (II) containing only one centre of asymmetry may be resolved in known manner, for example using an optically active acid as a resolving agent. Compounds of the formula (II) containing two centres of asymmetry may be separated into their diastereoisomers by fractional crystallisation from a suitable solvent, for example from ethyl acetate. After such separation the individual components of the diastereoisomer may be obtained by resolution in known manner, for example using an optically active acid as a resolving agent.

Suitable optically active acids for use in resolution processes are described in Topics In Stereochemistry, Vol. 6, Wiley Interscience 1971, Allinger N. L. and Eliel W. L. eds.

Stereospecific synthesis may also be employed in order to obtain specific enantiomers. Thus, for example a single enantiomer of a compound of the formula (VI) may be used to react with a compound of the formula (VII) prior to borohydride or catalytic reduction. Similarly a single enantiomer of a compound of the formula (VIII) may be used with a compound of the formula (IX). Similarly a single enantiomer of a compound of the formula (IX) (where $R_4$ is not the same as $R_5$) may be used to react with a compound of the formula (XI) prior to borohydride reduction. The specific enantiomers produced by these processes may then be separated by conventional means such as fractional crystallisation from a suitable solvent, for example ethyl acetate.

The following Examples illustrate the invention; and the following Descriptions illustrate the preparation of useful intermediates.

EXAMPLE 1

N-[2-(4-Carbomethoxymethoxyphenyl)-1-methylethyl]-2-hydroxy-2-(4-hydroxy-3-hydroxymethylphenyl)ethanamine A mixture of 1-(4-carbomethoxymethoxyphenyl)propan-2-one (1.5 g) and 2-hydroxy-2-(4-hydroxy-3-hydroxymethylphenyl)ethanamine (1.23 g) in ethanol (80 ml) was refluxed 0.5 hours, cooled to ambient temperature, 10% Pd/C added and the mixture hydrogenated at 75 psi and 50°-60° for 8 hours. The solution was filtered, evaporated, the residue taken up in ethyl acetate and filtered again. Removal of the solvent gave an oil which was crystallised and recrystallised from benzene to give the title compound, 0.47 g, mp 60°-63° as a 52:48 mixture of diastereoisomers. $\tau(d_6DMSO)$ 9.1 (3H, d, J=6 Hz), 6.6-7.8 (5H, m), 6.4 (3H, s), 5.72 (1H, t, J=6 Hz), 5.54 (2H, s), 5.3 (2H, s), 7.2-6.4 (7H, m), 7.6-5.5 (4H, broad, disappears with $D_2O$).

EXAMPLE 2

N-[2-(4-(1-Carboethoxy)ethoxyphenyl)-1-methylethyl]-2-hydroxy-2-(4-hydroxy-3-hydroxymethylphenyl)ethanamine The compound was prepared as in Example 1 from 1-(4-(1-carboethoxy)ethoxyphenyl) propan-2-one (1.22 g) and 2-hydroxy-2-(4-hydroxy-3-hydroxymethylphenyl) ethanamine (0.95 g), and crystallised from benzene m.p. 53°-55° as a 53:47 mixture of diastereoisomers.

$\tau(d_6DMSO)$ 9.05 (3H, d, J=6 Hz), 8.80 (3H, t, J=8 Hz), 8.46 (3H, d, J=6 Hz), 6.9-7.8 (5H, m), 5.84 (2H, q, J=8 Hz), 5.46 (2H, s), 5.12 (1H, d, J=6 Hz), 4.0-6.0 (5H, broad, 4H replaceable by $D_2O$), 2.4-3.4 (7H, m).

EXAMPLE 3

N-[2-(4-(1-Carboethoxy-1-methyl)ethoxyphenyl)-1-methylethyl]-2-hydroxy-2-(4-hydroxy-3-hydroxymethylphenyl) ethanamine The compound was prepared as in Example 1 from 1-(4-(1-carboethoxy-1-methyl) ethoxyphenyl) propan-2-one (1.75 g) and 2-hydroxy-2-(4-hydroxy-3-hydroxymethylphenyl) ethanamine (1.21 g), and crystallised from benzene m.p. 82°-87° as a 52:48 mixture of diastereoisomers.

$\tau(d_6DMSO)$ 9.13 (3H, d, J=6 Hz), 8.87 (3H, t, J=8 Hz) 8.50 (6H, s), 7.1-7.8 (5H, m), 5.9 (2H, q, J=8 Hz), 5.6 (2H, s), 5.6 (1H, m), 2.7-3.5 (7H, m), 5.0-7.7 (4H, broad, disappears with $D_2O$).

EXAMPLE 4

N-[2-(3-Carbomethoxymethoxyphenyl)-1-methylethyl]-2-hydroxy-2-(4-hydroxy-3-hydroxymethylphenyl) ethanamine The compound was prepared as in Example 1 from 1-(3-carbomethoxymethoxyphenyl) propan-2-one (1.82 g) and 2-hydroxy-2-(4-hydroxy-3-hydroxymethylphenyl) ethanamine (1.5 g) and crystallised from benzene m.p. 60°-64° as a 42:58 mixture of diastereoisomers.

$\tau(d_6DMSO)$ 9.1 (3H, d, J=6 Hz), 7.0-7.7 (5H, m), 6.32 (3H, s), 5.5 (2H, s), 5.5 (1H, m), 5.3 (2H, s), 2.6-3.6 (7H, m), 4.5-8.1 (4H, broad, disappears with $D_2O$).

EXAMPLE 5

N-[2-(4-(3-Carbomethoxyprop-2-eneoxy)phenyl)-1-methylethyl]-2-hydroxy-2-(4-chlorophenyl) ethanamine A mixture of 1-(4-(3-carbomethoxyprop-2-eneoxy)phenyl) propan-2-one (2.27 g) and 2-hydroxy-2-(4-chlorophenyl) ethanamine (1.57 g) in benzene (100 ml) was boiled under reflux with azeotropic removal of water using a Dean and Stark trap. The solution was evaporated, the residue dissolved in methanol (50 ml), cooled in ice and sodium borohydride added. The solution was stirred for 1 hour at 0° C., the methanol evaporated, and the residue partitioned between water and ethyl acetate. The ethyl acetate layer was dried ($MgSO_4$) and evaporated to give a cream solid (3.1 g) which was crystallised from ethyl acetate m.p. 120°-122°. as a 0:100 mixture of diastereoisomers. Recrystallisation of the mother liquors from hexane gave a 70:30 mixture of diastereoisomers, m.p. 55°-65°.

$\tau(CDCl_3)$ 8.98 (3H, d, J=6 Hz), 6.9-7.7 (7H, m), 6.3 (3H, s), 5.4 (1H, m), 5.38 (2H, m), 3.85 (1H, dt, J=6 Hz, J=2 Hz), 3.2 (2H, d, J=8 Hz), 3.0 (2H, d, J=8 Hz), 2.9 (1H, dt, J=16 Hz, J=2 Hz), 2.8 (4H, s).

EXAMPLE 6

N-[2-(4-Carbomethoxymethoxyphenyl)-1-methylethyl]-2-hydroxy-2-(3-chlorophenyl) ethanamine The compound was prepared as in Example 5 from 1-(4-carbomethoxymethoxyphenyl)propan-2-one (2.22 g) and 2-hydroxy-2-(3-chlorophenyl) ethanamine (1.71 g) and crystallised from hexane m.p. 82°-87° as a 58:42 mixture of diastereoisomers.

$\tau(CDCl_3)$ 8.95 (3H, d, J=6 Hz), 6.8-7.6 (7H, m), 6.24 (3H, s), 5.4 (2H, s), 5.4 (1H, m), 2.6-3.3 (7H, m).

EXAMPLE 7

N-[2-(4-Carbomethoxymethoxyphenyl)-1-methylethyl]-2-hydroxy-2-phenyl ethanamine

The compound was prepared as in Example 1 from 1-(4-carbomethoxymethoxyphenyl)propan-2-one (4.1 g) and 2-hydroxy-2-phenylethylamine (2.53 g). The compound was purified initially by column chromatography on silica gel and crystallised as the hydrobromide salt from methanol/diethyl ether m.p. 147°–160° as a 90:10 mixture of diastereoisomers.

$\tau(CDCl_3)$—free base—8.9 (3H, d, J=6 Hz), 6.9–7.6 (7H, m), 6.25 (3H, s), 5.4 (2H, s), 5.4 (1H, m), 3.2 (2H, d, J=8 Hz), 2.9 (2H, d, J=8 Hz), 2.7 (5H, s).

EXAMPLE 8

N-[2-(4-Carbomethoxymethoxyphenyl)-1-methylethyl]-2-hydroxy-2-(3-trifluoromethylphenyl) ethanamine The compound was prepared as in Example 5 from 1-(4-carbomethoxymethoxyphenyl)propan-2-one (2.22 g) and 2-hydroxy-2-(3-trifluoromethylphenyl) ethanamine (2.05 g). The compound crystallised from hexane m.p. 70°–85° as a 1:1 mixture of diastereoisomers.

$\tau(CDCl_3)$ 8.95 (3H, d, J=6 Hz), 6.8–7.7 (7H, m), 6.22 (3H, s), 5.4 (2H, s), 5.4 (1H, m), 3.2 (2H, dd, J=8 Hz, J=2 Hz), 2.9 (2H, dd, J=8 Hz, J=2 Hz), 2.3–2.7 (4H, m).

EXAMPLE 9

N-[2-(4-(3-Carbomethoxypropoxy)phenyl)-1-methylethyl]-2-hydroxy-2-phenylethanamine The compound was prepared as in Example 5 from 1-(4-(3-carbomethoxypropoxy)phenyl] propan-2-one (6.0 g) and 2-hydroxy-2-phenyl ethanamine (3.29 g) and crystallised from hexane m.p. 60°–76° as a 1:1 mixture of diastereoisomers.

$\tau(CDCl_3)$ 8.95 (3H, d, J=6 Hz), 7.9 (2H, m), 6.95–7.65 (9H, m, 2 replaceable by $D_2O$), 6.35 (3H, s), 6.1 (2H, t, J=6 Hz), 5.4 (1H, m), 3.25 (2H, d, J=8 Hz), 3.0 (2H, dd, J=8 Hz, 2 Hz), 2.7 (5H, s).

EXAMPLE 10

N-[2-(4-Carboxmethoxyphenyl)-1-methylethyl]-2-hydroxy-2-phenylethanamine sodium salt A solution of N-[2-(4-carbomethoxymethoxyphenyl)-1-methylethyl]-2-hydroxy-2-phenylethanamine (1 g) in methanol (10 ml) was added to a solution of sodium hydroxide (116 mg) in water (20 ml) and the solution boiled under reflux for 12 hours. The mixture was evaporated to dryness to give a yellow solid (1 g). The compound crystallised as a 1:1 mixture of diastereoisomers.

$\tau(d_6DMSO)$ 9.15 (3H, d, J=6 Hz), 7.1–7.6 (5H, m), 6.4–7.0 (2H, broad, replaceable by $D_2O$), 5.95 (2H, s), 5.5 (1H, m), 3.3 (2H, dd, J=8 Hz, J=2 Hz), 3.04 (2H, dd, J=8 Hz, J=2 Hz), 2.7 (5H, s).

EXAMPLE 11

N-[2-(4-Carbamoylmethoxyphenyl)-1-methylethyl]-2-hydroxy-2-phenylethanamine

A solution of N-[2-(4-carbomethoxymethoxyphenyl)-1-methylethyl]-2-hydroxy-2-phenylethanamine (0.5 g) in methanol (10 ml) was treated with a solution of 0.880 ammonia (40 ml), the resulting mixture boiled for 1½ hours then stirred at ambient temperature for 18 hours. The resulting white precipitate was filtered off to yield the title compound (0.17 g) m.p. 158°–162°, as an 82:18 mixture of diastereoisomers.

$\tau(d_6DMSO)$ 9.11 (3H, d), 7.12–7.80 (5H, m), 6.41–7.08 (1H, broad), 5.67 (2H, s), 5.47 (1H, t), 4.56–5.20 (1H broad), 2.50–3.30 (11H, m).

EXAMPLE 12

N-[2-(4-N-Methylcarbamoylmethoxyphenyl)-1-methylethyl]-2-hydroxy-2-phenylethanamine A solution of N-[2-(4-carbomethoxymethoxyphenyl)-1-methylethyl]-2-hydroxy-2-phenylethanamine (0.5 g) in methanol (5 ml) was treated with a 25% solution of methylamine in water (80 ml), the resulting solution boiled for 1½ hours then stirred at ambient temperature for 18 hours. The solution was extracted with chloroform and the organic extracts washes with water, dried ($MgSO_4$) and evaporated to yield an oil which on trituration yielded the title compound as a white solid (0.24 g) m.p. 98°–110°, as a 65:35 mixture of diastereoisomers.

$\tau(d_6DMSO)$ 9.13 (3H, d, J=6 Hz), 7.25–7.75 (8H, m), 6.6–7.0 (1H, broad), 5.63 (2H, s), 5.50 (1H, t), 4.7–5.2 (1H, broad), 2.62–3.30 (9H, m), 1.9–2.3 (1H, broad).

EXAMPLE 13

N-[2-(4-Carbomethoxymethoxyphenyl)-1-methylethyl]-2-hydroxy-2-(2-fluorophenyl) ethanamine The compound was prepared as in Example 5 from 1-(4-carbomethoxymethoxyphenyl) propan-2-one (2.22 g) and 2-hydroxy-2-(2-fluorophenyl) ethanamine (1.55 g), and crystallised from hexane m.p. 60°–80° as a 55:45 mixture of diastereoisomers.

$\tau(CDCl_3)$ 8.95 (3H, d, J=6 Hz), 6.8–7.6 (5H, m), 6.25 (3H, s), 5.42 (2H, s), 5.15 (1H, m), 2.4–3.3 (8H, m), 7.0–8.0 (2H, broad, replaceable by $D_2O$).

EXAMPLE 14

N-[3-(4-Carbomethoxymethoxyphenyl)-1-(S)-1-methylpropyl]-2-hydroxy-2-phenylethanamine A mixture of 3-(4-carbomethoxymethoxyphenyl)-1-(S)-1-methylpropylamine (1.6 g) and phenylglyoxal-monohydrate (1.03 g) in benzene (70 ml) was boiled under reflux with azeotropic removal of water for 3 hours. After cooling to ambient temperature, the benzene was evaporated, the residue dissolved in methanol (30 ml), cooled to 0° C. and sodium borohydride (0.5 g) added. After ten minutes, the solvent was evaporated, and the residual solid partitioned between water and ether. The ether layer was dried ($MgSO_4$) and evaporated to leave an oil. Crystallisation from hexane gave a white solid (70 mg) m.p. 61°–65° as a 50:50 mixture of diastereoisomers.

$\tau(CDCl_3)$, 8.95 (3H, d, J=6 Hz), 8.35 (2H, m), 7.0–8.0 (2H, broad), 7.4 (2H, m), 7.15 (1H, m), 6.27 (3H, s), 5.4 (2H, s+1H m), 3.25 (2H, d, J=8 Hz), 2.9 (2H, d, J=8 Hz), 2.65 (5H, m).

EXAMPLE 15

N-[2-(4-Carbomethoxymethoxyphenyl)-1-(S)-1-methylethyl]-2-hydroxy-2-phenylethanamine The title compound was prepared as in Example 14 from 2-(4-carbomethoxymethoxyphenyl)-1-(S)-1-methylethylamine (1.4 g) and phenylglyoxal monohydrate (0.96 g). Crystallisation from hexane gave a white solid m.p. 78°–81° as a mixture of diastereoisomers.

$\tau(CDCl_3)$ 8.95 (3H, d, J=6 Hz), 6.95–8.0 (5H, m; 2H, broad, replaceable by $D_2O$), 6.21 (3H, s), 5.40 (2H, s), 5.4 (1H, m), 3.20 (2H, d, J=8 Hz), 2.94 (2H, d, J=8 Hz), 2.70 (5H, s).

DESCRIPTION 1

1-(4-Carbomethoxymethoxyphenyl)propan-2-one

Sodium metabisulphite (26 g) in water (60 ml) was added to 1-(4-carbomethoxymethoxyphenyl)propan-2-one oxime (7.5 g) in methanol (50 ml) and the mixture refluxed for 6 hours. The reaction mixture was cooled, concentrated hydrochloric acid (30 ml) added and the mixture extracted with ethyl acetate. The combined ethyl acetate extracts were washed with water followed by sodium bicarbonate solution. The ethyl acetate layer was dried (MgSO$_4$) and evaporated to give the title compound as an oil which crystallised on standing, (mp 63°–70°1). $\tau$ (CDCl$_3$) 7.91 (3H, s), 6.30 (2H, s), 6.26 (3H, s), 5.42 (2H, s), 3.17 (2H, d, J=8 Hz), 2.87 (2H, d, J=8 Hz).

DESCRIPTION 2

1-(4-Carbomethoxymethoxyphenyl)propan-2-one oxime 1-(4-Carbomethoxymethoxyphenyl)-2-nitroprop-1-ene (8.7 g) in tetrahydrofuran (100 ml) was stirred with aluminium amalgam, made in the normal way from aluminium (6 g) and mercuric chloride (3 g). The mixture was cooled in ice and stirring was continued until reaction was complete. The slurry was filtered through celite and the filtrate was evaporated to give a cream solid (7.5 g). $\tau$(CDCl$_3$) 8.24 (3H, s), 6.36 (2H, s), 6.24 (3H, s), 5.43 (2H, s), 3.20 (2H, d, J=8 Hz), 2.83 (2H, d, J=8 Hz), 2.5–3.4 (1H, broad, disappears with D$_2$O).

DESCRIPTION 3

1-(4-Carbomethoxymethoxyphenyl)-2-nitroprop-1-ene

4-Carbomethoxymethoxybenzaldehyde (10.2 g) and n-butylamine (7.2 ml) were heated in refluxing benzene (100 ml) under a Dean and Stark head until the theoretical amount of water had been collected. The benzene was evaporated and the residual oil was taken up in glacial acetic acid (30 ml). Nitroethane (9.3 ml) was added and the mixture was stirred and heated at 95°–105° for 1 hour. The product crystallised on cooling (11.0 g). $\tau$(CDCl$_3$) 7.58 (3H, s), 6.20 (3H, s), 5.30 (2H, s), 3.02 (2H, d, J=8 Hz), 2.55 (2H, d, J=8 Hz), 1.97 (1H, s).

DESCRIPTION 4

1-[4-(1-Carboethoxy) ethoxyphenyl]propan-2-one

To a solution of sodium (370 mg) in ethanol (100 ml) was added 4-hydroxyphenylpropan-2-one ethylene ketal (3.14 g), ethyl 2-bromo propionate (2.93 g), and the mixture heated under reflux for 8 hours. The solvent was evaporated, the residue dissolved in a mixture of 2.5 N hydrochloric acid (20 ml) and ethanol (70 ml), and the solution stirred at ambient temperature for 16 hours. The solvent was evaporated, the residue dissolved in dichloromethane, washed successively with 2 N sodium hydroxide, water, dried (MgSO$_4$) and evaporated to give the title compound (1.5 g) as a yellow oil.

$\tau$(CDCl$_3$) 8.75 (3H, t, J=6 Hz), 8.4 (3H, d, J=6 Hz), 7.95 (3H, s), 6.45 (2H, s), 5.8 (2H, q, J=6 Hz), 5.3 (1H, q, J=6 Hz), 3.2 (2H, d, J=8 Hz), 2.9 (2H, d, J=8 Hz).

DESCRIPTION 5

1-[4-(1-Carboethoxy-1-methyl) ethoxyphenyl]propan-2-one

The title compound was prepared as in Description 4 from 4-hydroxyphenylpropan-2-one ethylene ketal (1.94 g) and ethyl-2-bromo-isobutyrate (1.95 g) as a yellow oil.

$\tau$(CDCl$_3$) 8.8 (3H, t, J=6 Hz), 8.4 (6H, s), 7.9 (3H, s), 6.4 (2H, s), 5.8 (2H, q, J=6 Hz), 3.2 (2H, d, J=8 Hz), 2.9 (2H, d, J=8 Hz).

DESCRIPTION 6

1-(3-Carbomethoxymethoxyphenyl)propan-2-one

The title compound was prepared as in Description 1 from 1-(3-carbomethoxymethoxyphenyl) propan-2-one oxime (9 g) as an oil (6.7 g). b.p. 170°–173° (3 mm).

$\tau$(CDCl$_3$) 7.9 (3H, s), 6.4 (2H, s), 6.3 (3H, s), 5.44 (2H, s), 2.7–3.4 (4H, m).

DESCRIPTION 7

1-[4-(3-Carbomethoxyprop-2-eneoxy)phenyl]propan-2-one

A mixture of 4-hydroxyphenylpropan-2-one ethylene ketal (3.0 g) and potassium carbonate (2.13 g) in acetone (50 ml) was treated with methyl 4-bromocrotonate (2.77 g) and a trace of potassium iodide. After heating under reflux for 12 hours, the solution was filtered, the solvent evaporated and the residue dissolved in methanol (50 ml) and 2.5 N hydrochloric acid (25 ml). The solution was stirred at ambient temperature for 2 hours, the solvent evaporated, the residue extracted with ether, washed with 2 N sodium hydroxide, water and dried (MgSO$_4$). Removal of the solvent gave the title compound as an oil (2.3 g).

$\tau$(CDCl$_3$) 7.9 (3H, s), 6.4 (2H, s), 6.3 (3H, s), 5.4 (2H, dd, J=2 Hz, J=2 Hz), 3.85 (1H, dt, J=16 Hz, J=2 Hz, J=2 Hz), 2.7–3.3 (5H, m).

DESCRIPTION 8

1-[4-(3-Carbomethoxypropoxy) phenyl]propan-2-one

To a solution of 1-[4-(3-carbomethoxyprop-2-eneoxy)phenyl]propan-2-one (1.1 g) in ethanol (50 ml), was added 10% Pd/C (100 mg) and the mixture hydrogenated at ambient temperature and atmospheric pressure until hydrogen uptake was complete (approx. 10 minutes). The solution was filtered, evaporated to give the title compound (1.1 g) as an oil.

$\tau$(CDCl$_3$) 7.9 (3H, s), 7.9 (2H, m), 7.5 (2H, t, J=6 Hz), 6.44 (2H, s), 6.35 (3H, s), 6.02 (2H, t, J=6 Hz), 2.8–3.3 (4H, m).

DESCRIPTION 9

1-(4-Benzyloxyphenyl) propan-2-one

The title compound was prepared as in Description 1 from 1-(4-benzyloxyphenyl) propan-2-one oxime (18.8 g) as an oil (16.4 g) b.p. 195°–200° C. (1.5 mm) which crystallised on standing m.p. 50°–54°.

$\tau$(CDCl$_3$) 7.9 (3H, s), 6.4 (2H, s), 4.98 (2H, s), 3.05 (2H, d, J=8 Hz), 2.85 (2H, d, J=8 Hz), 2.6 (5H, s).

15

DESCRIPTION 10

1-(4-Benzyloxyphenyl) propan-2-one oxime

The title compound was prepared as in Description 2 from 1-(4-benzyloxyphenyl)-2-nitroprop-2-ene (21 g) as a light brown solid (18.8 g).

τ(CDCl$_3$) 8.28 (3H, s), 6.38 (2H, s), 5.1 (2H, s), 3.2 (2H, d, J=8 Hz), 2.9 (2H, d, J=8 Hz), 2.75 (5H, s), 0.1–1.2 (1H, broad, replaceable by D$_2$O).

DESCRIPTION 11

1-(3-Carbomethoxymethoxyphenyl)-2-nitroprop-1-ene

The title compound was prepared as in Description 3 from 3-carbomethoxymethoxybenzaldehyde (8.15 g) and isolated as a yellow crystalline solid m.p. 57°–61°.

τ(CDCl$_3$) 7.6 (3H, s), 6.23 (3H, s), 5.37 (2H, s), 2.3–3.2 (4H, m), 2.03 (1H, s).

DESCRIPTION 12

1-(4-Benzyloxyphenyl)-2-nitroprop-1-ene

The title compound was prepared as in Description 3 from 4-benzyloxybenzaldehyde (21.2 g) and isolated as a yellow crystalline solid (22 g), m.p. 142.5°–144.5°.

τ(C$_5$D$_5$N) 7.66 (3H, s), 4.85 (2H, s), 2.2–3.0 (9H, m), 1.82 (1H, s).

DESCRIPTION 13

1-(4-Hydroxyphenyl)-2-nitroprop-1-ene

The title compound was prepared as in Description 3 from 4-hydroxybenzaldehyde (12.2 g) and isolated as a yellow crystalline solid (6.5 g) m.p. 125°–128°.

τ(CDCl$_3$) 7.6 (3H, s), 3.9 (1H, bs, replaceable by D$_2$O), 3.05 (2H, d, J=8 Hz), 2.6 (2H, d, J=8 Hz), 1.92 (1H, s).

DESCRIPTION 14

1-(4-Benzyloxyphenyl) propan-2-one ethylene ketal

A solution of 1-(4-benzyloxyphenyl) propan-2-one (5 g), ethylene glycol (1.4 g) and a trace amount of 4-toluenesulphonic acid, in benzene (100 ml) was heated under reflux with azetropic removal of water for 2 hours. The solvent was evaporated, the residue dissolved in ethyl acetate, washed with 1.2 N sodium bicarbonate solution, dried (MgSO$_4$) and evaporated to give a light brown oil which crystallised on standing (6.1 g) m.p. 58°–62°.

τ(CDCl$_3$) 8.72 (3H, s), 7.2 (2H, s), 6.1–6.4 (4H, m), 5.02 (2H, s) 3.15 (2H, d, J=8 Hz), 2.8 (2H, d, J=8 Hz), 2.5–2.8 (5H, m).

DESCRIPTION 15

1-(4-Hydroxyphenyl)propan-2-one ethylene ketal

A solution of 1-(4-benzyloxyphenyl) propan-2-one ethylene ketal (6 g) in ethanol (100 ml) was hydrogenated at 45 psi and ambient temperature in the presence of 10% Pd/C until hydrogen uptake had ceased. The solution was filtered and evaporated to give a light coloured oil which crystallised on standing m.p. 61°–64°.

τ(CDCl$_3$) 8.7 (3H, s), 7.2 (2H, s), 6.0–6.4 (4H, m), 3.4–3.9 (1H, broad, replaceable by D$_2$O), 3.35 (2H, d, J=8 Hz), 2.9 (2H, d, J=8 Hz).

DESCRIPTION 16

3-(4-Carbomethoxymethoxyphenyl)-1-(S)-1-methylpropylamine hydrochloride

To a solution of N-[3-(4-carbomethoxymethoxyphenyl)-1-methylpropyl]-1-(S)-1-methylbenzylamine hydrochloride (11.9 g) in methanol (100 ml) was added a slurry of 5% Pd/C in ethyl acetate, and the mixture hydrogenated at 50° C., 60 p.s.i. for 1 day. The solution was filtered, evaporated and the residue recrystallised from ethyl acetate to give the title compound (6.3 g) m.p. 118–122. [α]$_D^{20}$ −4.4 (HD$_2$O).

τ(d$_6$DMSO) 8.75 (3H, d, J=6 Hz), 7.9–8.5 (2H, m), 7.45 (2H, m), 6.9 (1H, m), 6.32 (3H, s), 5.3 (2H, s), 3.15 (2H, d, J=8 Hz), 2.87 (2H, d, J=8 Hz), 1.8 (3H, broad, disappears with D$_2$O).

DESCRIPTION 17

N-[3-(4-Carbomethoxymethoxyphenyl)-1-methylpropyl]-1-(S)-1-methylbenzylamine hydrochloride A solution of 4-(4-carbomethoxymethoxyphenyl) butan-2-one (19.4 g) and 1-(S)-1-methylbenzylamine (9.95 g) in benzene (200 ml) was heated under reflux for 3 hours with azeotropic removal of water. After cooling to ambient temperature, the benzene was evaporated, the residue dissolved in ethanol (200 ml) and hydrogenated in the presence of Raney nickel (10 ml) at 60 p.s.i. for 48 hours. The solution was filtered evaporated, the residual oil dissolved in ether and treated with a solution of ether/hydrogen chloride. The precipitated solid was recrystallised from ethyl acetate (11.9 g).

τ(d$_6$DMSO): 8.72 (3H, d, J=6 Hz), 8.4 (3H, d, J=6 Hz), 7.0–8.0 (5H, m), 6.35 (3H, s), 5.5 (1H, m), 5.3 (2H, s), 3.2 (2H, d, J=8 Hz), 3.0 (2H, d, J=8 Hz), 2.65 (3H, m), 2.4 (2H, m), 0.65 (1H, broad, disappears with D$_2$O), 0.1 (1H, broad, disappears with D$_2$O).

DESCRIPTION 18

4-(4-Carbomethoxymethoxyphenyl) butan-2-one

A solution of 4-(4-hydroxyphenyl) butan-2-one (16.4 g), methyl bromoacetate (15.3 g, 8.5 ml), potassium carbonate (13.8 g) and a trace of potassium iodide in acetone (200 ml) was heated under reflux for 16 hours. The solution was filtered, evaporated and the residue dissolved in ether. The ether solution was shaken successively with 2 N sodium hydroxide solution, water, dried (MgSO$_4$) and evaporated to give the title compound as an oil (19.5 g).

τ(CDCl$_3$) 7.9 (3H, s), 7.25 (2H, m), 6.25 (3H, s), 5.4 (2H, s), 3.2 (2H, d, J=8 Hz), 2.9 (2H, d, J=8 Hz).

DESCRIPTION 19

N-[2-(4-Carbomethoxymethoxyphenyl)-1-methylethyl]-1-(S)-1-methylbenzylamine hydrochloride The title compound was prepared as in Description 17 from 4-(4-carbomethoxymethoxyphenyl)propan-2-one (15 g) and 1-(S)-1-methylbenzylamine (8.18 g) as a white crystalline solid (5.6 g) m.p. 177°–182°.

τ(d$_6$DMSO) 8.90 (3H, d, J=6 Hz), 8.36 (3H, d, J=6 Hz) 6.5–7.4 (3H, m), 6.37 (3H, s), 5.45 (1H, m), 5.3 (2H, s), 3.2 (4H, m), 2.6 (3H, m), 2.35 (2H, m), 0.6 (1H, broad, disappears with D$_2$O), −0.2 (1H, broad, disappears with D$_2$O).

DESCRIPTION 20

2-(4-Carbomethoxymethoxyphenyl)-1-(S)-1-methylethylamine hydrochloride

The title compound was prepared as in Description 16 from N-[2-(4-carbomethoxymethoxyphenyl)-1-methylethyl]-1-(S)-1-methylbenzylamine hydrochloride (5 g) as a white crystalline solid (2.3 g) m.p. 96°–101°, $[\alpha]_D^{20}+16.9°$ (HD$_2$O).

τ(d$_6$DMSO) 8.9 (3H, d, J=6 Hz), 6.5–7.5 (3H, m), 6.33 (3H, s), 5.3 (2H, s), 3.12 (2H, d, J=8 Hz), 2.85 (2H, d, J=8 Hz), 1.7 (3H, broad, disappears with D$_2$O).

DEMONSTRATION OF EFFECTIVENESS OF COMPOUNDS

ANTI-OBESITY ACTIVITY

The compounds were dosed daily in water or carboxymethyl cellulose suspension to genetically obese mice by oral gavage for 28 days. At the end of the time the carcass composition was determined. The results obtained were as follows:

| COMPOUND OF EXAMPLE | DOSE mg/kg p.o. | g-LIPID PER MOUSE TREATED | CONTROL |
|---|---|---|---|
| 1 | 11 | 12.9 | 18.6 |
| 2 | 11.5 | 10.3 | 18.6 |
| 5 (mp. 120–122°) | 11 | 16.8 | 17.9 |
| 6 | 5.3 | 13.8 | 19.3 |

HYPOGLYCAEMIC ACTIVITY

Female CFLP mice, weighing approximately 25 g, were fasted for 24 hours prior to the study. The compounds under study were dosed orally (20 mg and 5 mg/kg) to each of 8 mice. 30 minutes later a blood sample (20 ml) was obtained from the tail for the analysis of blood glucose. Immediately after taking this blood sample, each mouse was given a glucose load (1 g/kg body weight subcutaneously). Blood samples were then obtained from each mouse at 30 minute intervals for 120 minutes.

Compounds that produced a significant (P<0.05) reduction of blood glucose, compared with control mice given water, at any time interval were considered active. The area under the blood glucose curve over the 2 hour period after giving the glucose load was calculated for each compound and compared with the value for control animals. Thus a compound would give a 100% reduction in the area under the blood glucose curve if the blood glucose was maintained at the same level as in untreated fasted animals. Reduction in the glucose curve of more than 100% indicate that a compound, in spite of being given a glucose load, maintained blood glucose levels below that found in control fasted mice.

| COMPOUND OF EXAMPLE | DOSE mg/kg p.o. | REDUCTION IN AREA UNDER BLOOD GLUCOSE CURVE (%) |
|---|---|---|
| 1 | 1 | 241 |

CARDIAC ACTIVITY

Rat hearts were perfused by the Langendorff procedure. Hearts were dissected free within 30 seconds of death and reverse perfused via the aorta and coronary vessels with Krebs-Ringer bicarbonate solution (pH 7.4 37° C.) gassed with 95% O$_2$:5% CO$_2$. The flow rate was between 8–12 mls/minute. Responses were obtained after injection of drug dissolved in isotonic saline into the perfusion media. Heart rate and tension were displayed on an Ormed MX2P recorder via a tension transducer and heart ratemeter.

Results are expressed as a percentage of the response due to salbutamol.

| COMPOUND OF EXAMPLE | DOSE ADDED (μg) | HEART TENSION | HEART RATE |
|---|---|---|---|
| 1 | 10 | 100 | 132 |
| 3 | 10 | 83 | 125 |
| 5 | 10 | 0 | 0 |
| 6 | 10 | 42 | 80 |
| 9 | 10 | 40 | 40 |
| 10 | 10 | 100 | 33 |
| 11 | 30 | 115 | 116 |
| 12 | 30 | 85 | 50 |

EFFECT ON ENERGY EXPENDITURE

The effectiveness of the compounds of Examples 1 to 15 on the energy expenditure of mice was demonstrated by means of the following procedure.

Female CFLP mice each weighing approximately 24 g, were given as much food and water as they wanted before and during the experiment. The compounds of Examples 1 to 15 were dissolved in water by addition of the same number of moles hydrochloric acid, and these solutions were dosed orally to each of 12 mice. A further 12 mice were dosed orally with water. The mice were placed in boxes through which air was drawn and the oxygen content of the air leaving the boxes was measured. The energy expenditure of the mice was calculated for 21 hours after dosing from the volume of air leaving the boxes and its oxygen content following the principles described by J. B. de V. Weir (J. Physiol. (London) (1949) 109, 1–9). The food intake of the mice was measured over this same period of 21 hours. The results are expressed as a percentage of the mean food intake or rate of energy expenditure of the mice dosed with water.

| COMPOUND OF EXAMPLE | DOSE mg/kg po | PERCENTAGE OF CONTROL VALUES | |
|---|---|---|---|
| | | ENERGY EXPENDITURE | FOOD INTAKE |
| 1 | 22 | 131 | 83 |
| 2 | 23 | 128 | 102 |
| 3 | 24 | 118 | 88 |
| 4 | 22 | 117 | 91 |
| 5 0:100* | 22.5 | 119 | 95 |
| 70:30 | 22.5 | 126 | 93 |
| 6 | 21 | 143 | 89 |
| 7 | 23.5 | 134 | 86 |
| 8 | 23 | | 88 |
| 9 | 21 | 124 | 86 |
| 10 | 19.5 | 124 | 88 |
| 11 | 18 | 127 | 89 |
| 12 | 19 | 127 | 86 |
| 13 | 20 | 129 | 68 |
| 14 | | | |
| 15 | | | |

*Percentage ratios of diastereoisomers.

Since the compounds increased the rate of energy expenditure but they did not increase food intake, they very probably decreased the energy content of the mice. This would normally be due to a reduction in the body lipid content of the mice. Food absorption is sufficiently efficient in mice that increased efficiency of absorption alone is unlikely to have provided the fuel for the increase in energy expenditure. The increased energy expenditure without increased food intake is a reliable indication of the effective anti-obesity properties of the compounds.

We claim:

1. A compound of the formula

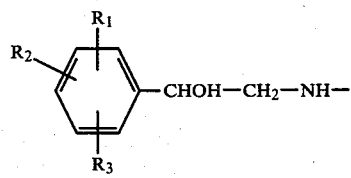

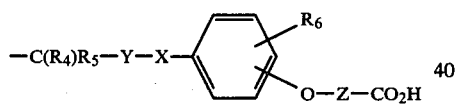

or a pharmaceutically acceptable salt, ester or amide thereof, in which $R_1$ is a hydrogen, fluoro, chloro, bromo, hydroxy, hydroxymethyl, methyl, methoxyl, amino, formamido, acetamido, methylsulphonylamido, nitro, benzyloxy, methylsulphonylmethyl, ureido, trifluoromethyl or p-methoxybenzylamino; $R_2$ is hydrogen, fluoro, chloro bromo or, hydroxy; $R_3$ is hydrogen, chloro bromo or hydroxy, $R_4$ is hydrogen or methyl; $R_5$ is hydrogen or methyl; $R_6$ is hydrogen, fluoro chloro, methyl, methoxyl or hydroxy; X is an oxygen atom or a carbon-carbon bond; Y is alkylene of up to 6 carbon atoms or a bond; and Z is alkylene, alkenylene or alkynylene of up to 10 carbon atoms.

2. A compound according to claim 1 in which $R_1$ is a hydrogen, fluoro, chloro bromo, trifluoromethyl, hydroxymethyl, hydroxyl or amino.

3. A compound according to claim 1 in which Y is methylene or ethylene.

4. A compound according to claim 1 in which $C(R_4)R_5$ is $CH_2$, —$CHCH_3$—, or $C(CH_3)_2$.

5. A compound according to claim 1 in which Z is —$(CH_2)_n$— in which n has a value of from 1 to 4.

6. A compound according to claim 1 in the form of a single stereoisomer.

7. A compound according to claim 1 in the form of a mixture of stereoisomers.

8. A compound according to claim 1 which contains two centres of asymmetry and is provided as a separated diastereoisomer.

9. A compound according to claim 1 of the formula:

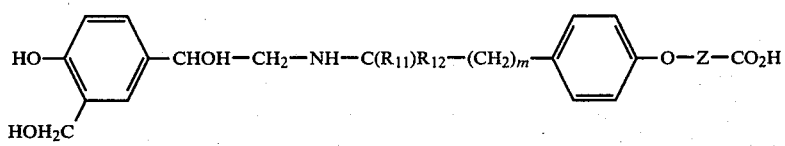

or a pharmaceutically acceptable salt, ester or amide thereof, wherein Z is alkylene, alkenylene or alkynylene of up to 10 carbon atoms, $R_{11}$ is hydrogen or methyl; $R_{12}$ is hydrogen or methyl; and m is 1, 2 or 3.

10. A compound according to claim 1 of the formula:

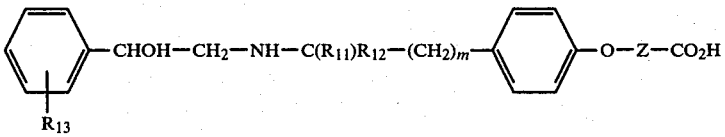

or a pharmaceutically acceptable salt, ester or amide thereof, wherein $R_{13}$ is hydrogen, fluoro, chloro or trifluoromethyl, Z is alkylene, alkenylene or alkynylene of up to 10 carbon atoms, $R_{11}$ is hydrogen or methyl; $R_{12}$ is hydrogen or methyl; and m is 1, 2 or 3.

11. A compound according to claim 10 in which Z is $CH_2$ group.

12. A compound of claim 1 selected from:
N-[2-(4-carbomethoxymethoxyphenyl)-1-methylethyl]-2-hydroxy-2-(4-hydroxy-3-hydroxymethylphenyl)ethanamine;
N-[2-(4-(1-carboethoxy)ethoxyphenyl)-1-methylethyl]-2-hydroxy-2-(4-hydroxy-3-hydroxymethylphenyl) ethanamine;
N-[2-(4-(1-carboethoxy-1-methyl)ethoxyphenyl)-1-methylethyl]-2-hydroxy-2-(4-hydroxy-3-hydroxymethylphenyl) ethanamine;
N-[2-(3-carbomethoxymethoxyphenyl)-1-methylethyl]-2-hydroxy-2-(4-hydroxy-3-hydroxymethylphenyl) ethanamine;
N-[2-(4-(3-carbomethoxyprop-2-eneoxy)phenyl)-1-methylethyl]-2-hydroxy-2-(4-chlorophenyl) ethanamine;
N-[2-(4-carbomethoxymethoxyphenyl)-1-methylethyl]-2-hydroxy-2-(3-chlorophenyl) ethanamine;
N-[2-(4-carbomethoxymethoxyphenyl)-1-methylethyl]-2-hydroxy-2-phenyl ethanamine;
N-[2-(4-carbomethoxymethoxyphenyl)-1-methylethyl]-2-hydroxy-2-(3-trifluoromethylphenyl) ethanamine;
N-[2-(4-(3-carbomethoxypropoxy)phenyl)-1-methylethyl]-2-hydroxy-2-phenylethanamine;
N-[2-(4-carboxymethoxyphenyl)-1-methylethyl]-2-hydroxy-2-phenylethanamine sodium salt;
N-[2-(4-carbamoylmethoxyphenyl)-1-methylethyl]-2-hydroxy-2-phenylethanamine;
N-[2-(4-N-methylcarbamoylmethoxyphenyl)-1-methylethyl]-2-hydroxy-2-phenylethanamine;
N-[2-(4-carbomethoxymethoxyphenyl)-1-methylethyl]-2-hydroxy-2-(2-fluorophenyl) ethanamine;

N-[3-(4-carbomethoxymethoxyphenyl)-1-(S)-1-methylpropyl]-2-hydroxy-2-phenylethanamine and
N-[2-(4-carbomethoxymethoxyphenyl)-1-(S)-1-methylethyl]-2-hydroxy-2-phenylethanamine.

13. An antiobesity pharmaceutical composition comprising an effective amount of a compound according to claim 1 and a pharmaceutically acceptable carrier.

14. A composition according to claim 13 in unit dosage form.

15. A composition according to claim 13 in the form of tablets, pills, capsules, ampoules or sachets.

16. A method of treating obesity or hyperglycaemia in human or non-human animals which comprises administering to the animals an effective amount of a compound according to claim 1.

* * * * *

UNITED STATES PATENT AND TRADEMARK OFFICE
CERTIFICATE OF CORRECTION

PATENT NO. : 4338333
DATED : July 6, 1982
INVENTOR(S) : ANTHONY TREVOR AINSWORTH, ET AL.

It is certified that error appears in the above-identified patent and that said Letters Patent are hereby corrected as shown below:

In the structural formula in the ABSTRACT, $(R_6)R_7$ should read: $(R_4)R_5$

Signed and Sealed this

Thirty-first Day of May 1983

[SEAL]

Attest:

DONALD J. QUIGG

Attesting Officer　　Acting Commissioner of Patents and Trademarks